(12) United States Patent
McCants et al.

(10) Patent No.: US 12,295,908 B2
(45) Date of Patent: May 13, 2025

(54) SCALP STIMULATION ASSEMBLY

(71) Applicants: Anne Dani McCants, Aurora, CO (US); Antoine McCants, Aurora, CO (US)

(72) Inventors: Anne Dani McCants, Aurora, CO (US); Antoine McCants, Aurora, CO (US)

( * ) Notice: Subject to any disclaimer, the term of this patent is extended or adjusted under 35 U.S.C. 154(b) by 765 days.

(21) Appl. No.: 17/551,962

(22) Filed: Dec. 15, 2021

(65) Prior Publication Data
US 2023/0181413 A1 Jun. 15, 2023

(51) Int. Cl.
*A61H 7/00* (2006.01)
*A61H 23/02* (2006.01)

(52) U.S. Cl.
CPC ............. *A61H 7/003* (2013.01); *A61H 23/02* (2013.01); *A61H 2201/0153* (2013.01); *A61H 2201/10* (2013.01); *A61H 2201/1638* (2013.01); *A61H 2201/1692* (2013.01); *A61H 2201/5025* (2013.01); *A61H 2201/5033* (2013.01); *A61H 2205/021* (2013.01)

(58) Field of Classification Search
CPC .......... A61H 2205/021; A61H 2201/10; A61H 2201/0169; A61H 2201/01638; A61H 7/003; A61N 2005/0661; A45D 24/00; A46B 17/02; A46B 2200/102; A46B 2200/306; A46B 2200/1093
See application file for complete search history.

(56) References Cited

U.S. PATENT DOCUMENTS

| | | | | |
|---|---|---|---|---|
| 2,958,086 A * | 11/1960 | Scully | ...................... | A47K 7/02 15/160 |
| 4,407,148 A * | 10/1983 | Rousseau | ............... | A44B 15/00 24/576.1 |
| 6,981,953 B1 * | 1/2006 | Ko | ..................... | A61H 15/0092 601/72 |
| 7,722,655 B2 * | 5/2010 | Lee | ...................... | A61N 5/0617 607/88 |
| 7,814,601 B2 | 10/2010 | Taggart | | |
| D629,209 S | 12/2010 | Taggart | | |
| 9,333,371 B2 * | 5/2016 | Bean | ........................ | A61N 7/02 |
| 11,648,415 B2 * | 5/2023 | Dijkstra | ................ | A61K 35/16 601/17 |

(Continued)

FOREIGN PATENT DOCUMENTS

| | | | | |
|---|---|---|---|---|
| KR | 101076057 | B1 * | 10/2011 | |
| WO | WO-2015137592 | A1 * | 9/2015 | ............. A45D 24/22 |
| WO | WO2017105123 | | 6/2017 | |

*Primary Examiner* — Brandy S Lee
*Assistant Examiner* — Mishal Zahra Hussain

(57) ABSTRACT

A scalp stimulation assembly includes a panel that can be rubbed along a user's scalp when the user is bathing. A plurality of light emitters is each of the light emitters is coupled to the panel to emit light onto the user's scalp when the panel is rubbed along the user's scalp. Each of the light emitters has an operational frequency in the ultraviolet spectrum to stimulate hair growth on the user's scalp when the panel is rubbed along the user's scalp. A plurality of domes is each of the domes is coupled to the panel to frictionally engage the user's scalp when the panel is rubbed along the user's scalp for stimulating hair growth. A vibration unit is integrated into the panel to physically stimulate the user's scalp when the panel is rubbed along the user's scalp.

7 Claims, 6 Drawing Sheets

(56) References Cited

U.S. PATENT DOCUMENTS

| | | | |
|---|---|---|---|
| 2007/0149900 A1* | 6/2007 | Lin | A61H 7/006 601/136 |
| 2009/0147081 A1 | 6/2009 | Hanson | |
| 2012/0167353 A1* | 7/2012 | Geller | G03B 17/561 24/302 |
| 2018/0360203 A1 | 12/2018 | Lee | |
| 2019/0075922 A1 | 3/2019 | Rivera | |
| 2020/0196936 A1 | 6/2020 | Blank | |

* cited by examiner

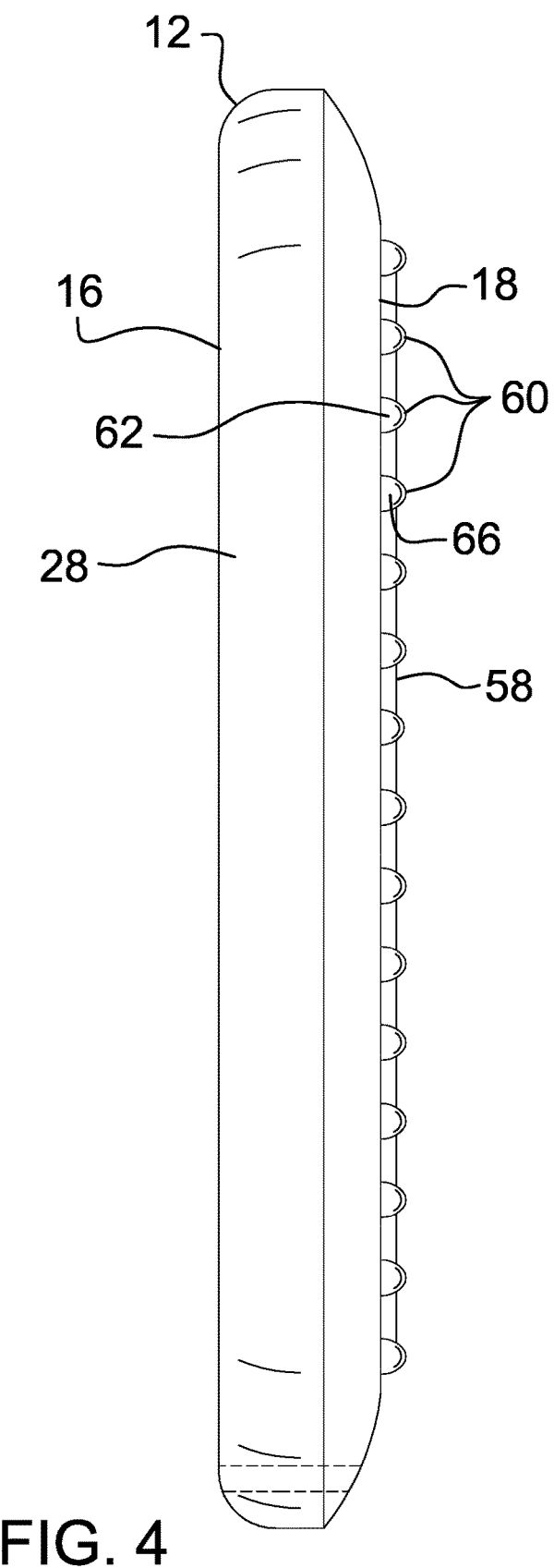
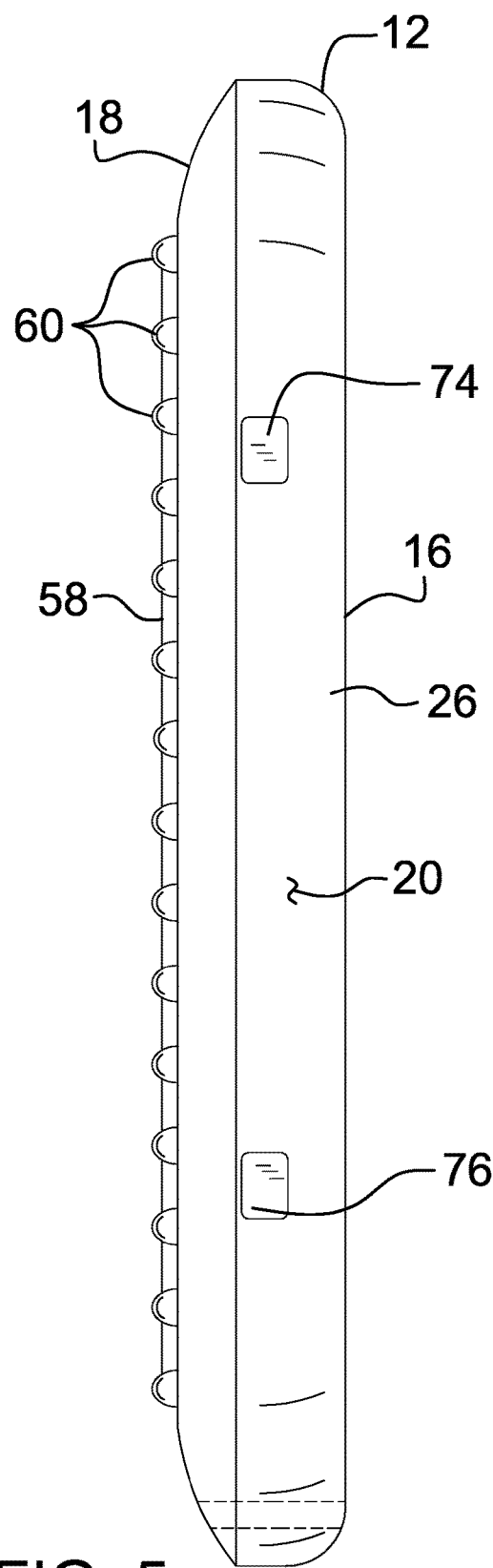
FIG. 4
FIG. 5

SCALP STIMULATION ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to stimulation devices and more particularly pertains to a new stimulation device for stimulating a user's scalp for promoting hair growth. The device includes a panel, a plurality of ultraviolet light emitters coupled to the panel and a plurality of domes coupled to the panel. The domes frictionally engage the user's scalp and the ultraviolet light emitters emit ultraviolet light onto the user's scalp when the panel is rubbed along the user's scalp. Additionally, the device includes a vibration unit that is integrated into the panel for stimulating the user's scalp.

(2) Description of Related Art Including Information Disclosed Under 37 CFR 1.97 and 1.98

The prior art relates to stimulation devices including a vibrating hair brush for stimulating a user's scalp. The prior art discloses a hair brush device that includes a light emitter for illuminating a user's scalp. The prior art discloses a variety of hair brush devices that each includes an air blower for blowing air onto a user's scalp. In no instance does the prior art disclose a scalp stimulator that includes ultraviolet light emitters and domes for physically stimulating a user's scalp.

BRIEF SUMMARY OF THE INVENTION

An embodiment of the disclosure meets the needs presented above by generally comprising a panel that can be rubbed along a user's scalp when the user is bathing. A plurality of light emitters is each of the light emitters is coupled to the panel to emit light onto the user's scalp when the panel is rubbed along the user's scalp. Each of the light emitters has an operational frequency in the ultraviolet spectrum to stimulate hair growth on the user's scalp when the panel is rubbed along the user's scalp. A plurality of domes is each of the domes is coupled to the panel to frictionally engage the user's scalp when the panel is rubbed along the user's scalp for stimulating hair growth. A vibration unit is integrated into the panel to physically stimulate the user's scalp when the panel is rubbed along the user's scalp.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 4 is a left side view of an embodiment of the disclosure.

FIG. 5 is a right side view of an embodiment of the disclosure.

DETAILED DESCRIPTION OF THE INVENTION

Figure 1:
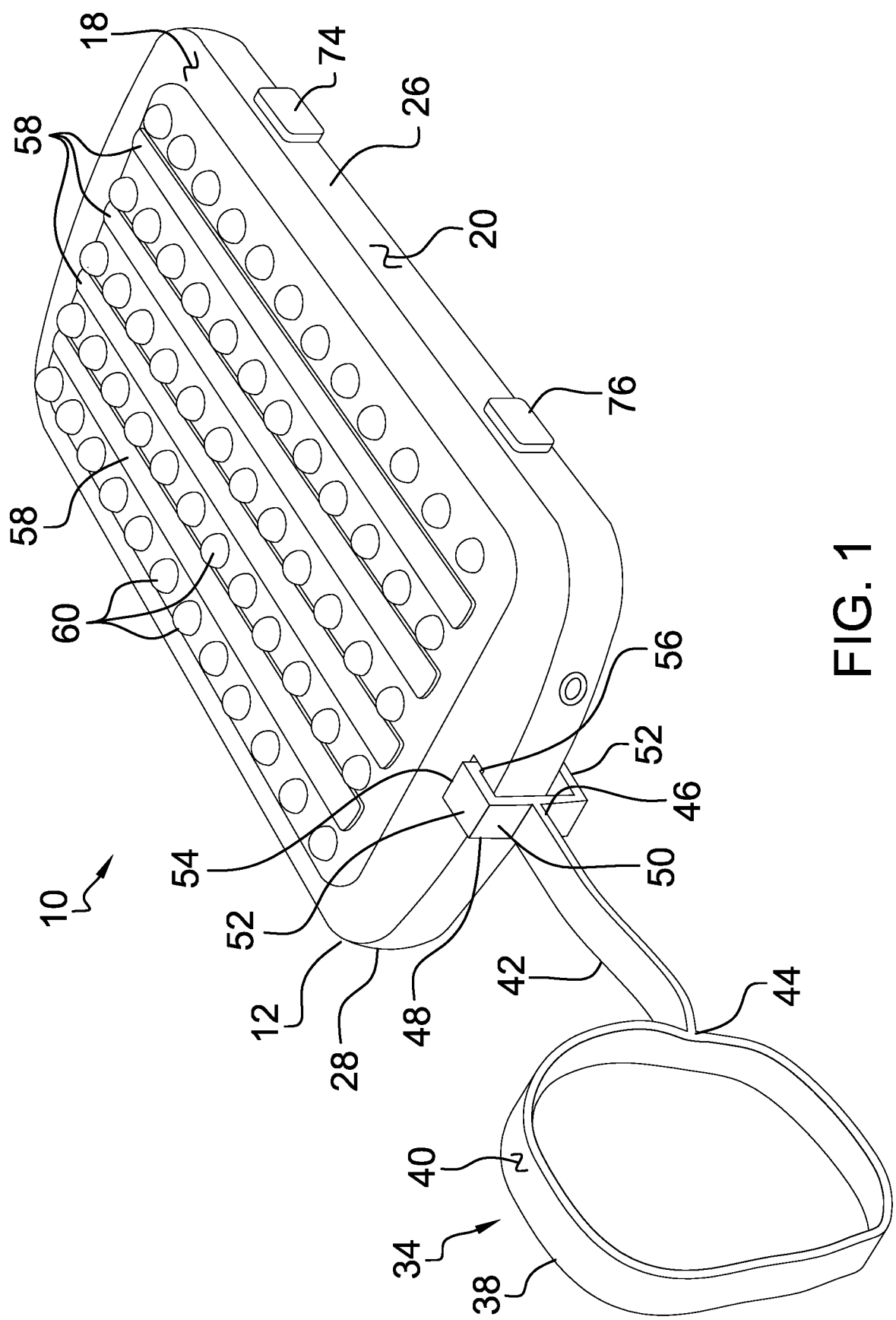
FIG. 1 is a perspective view of a scalp stimulation assembly according to an embodiment of the disclosure.
Figure 2:
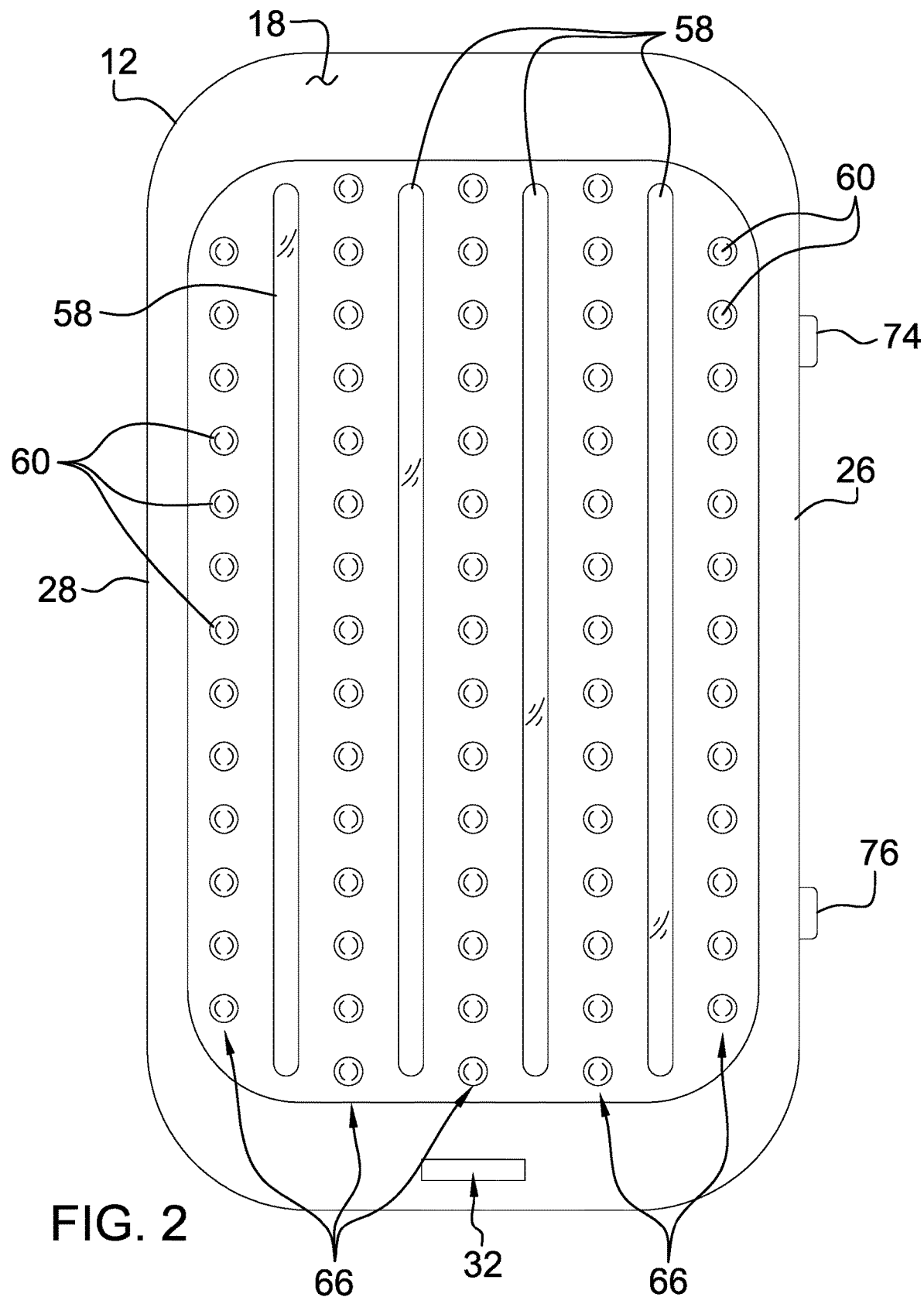
FIG. 2 is a bottom view of an embodiment of the disclosure.
Figure 3:
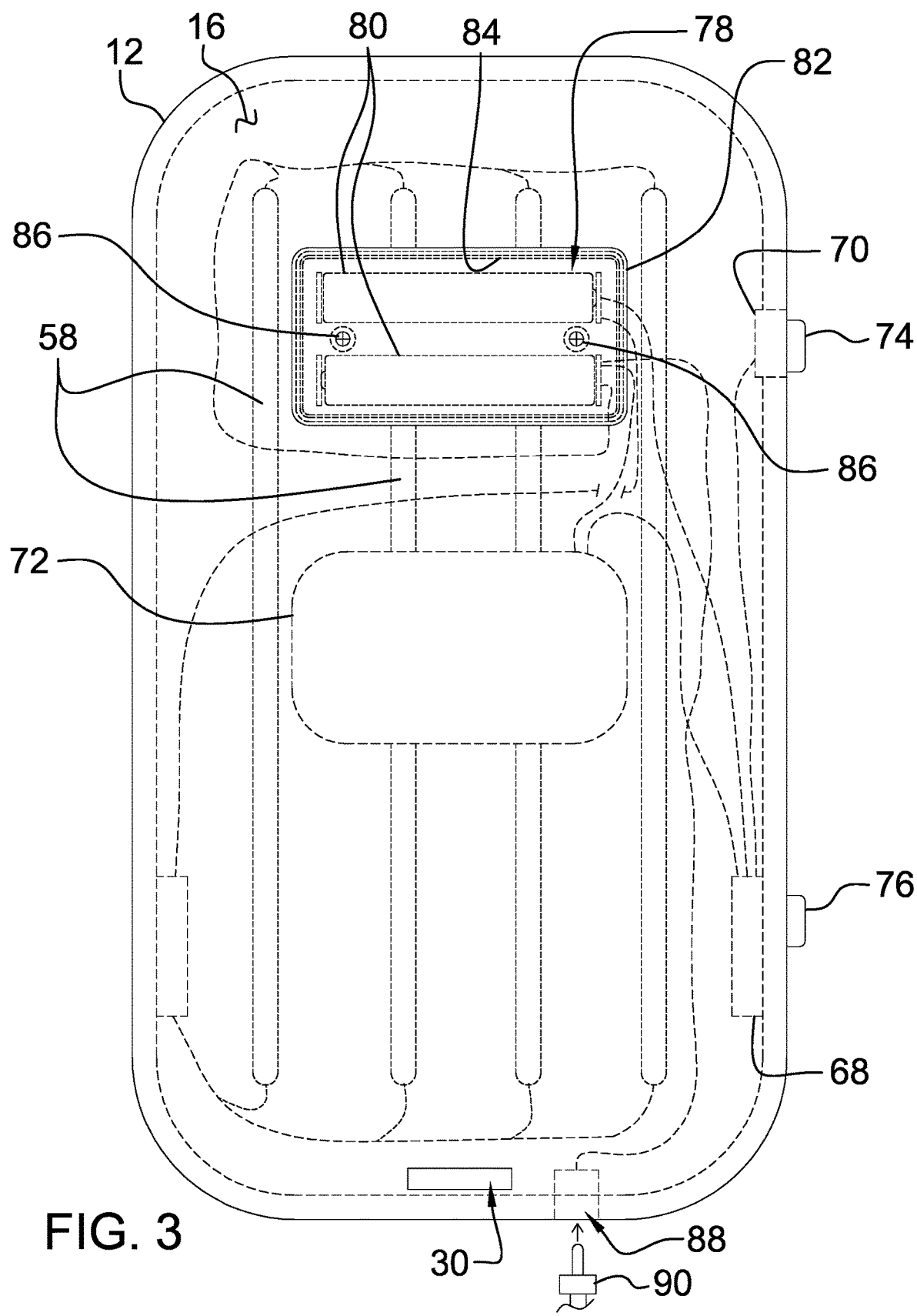
FIG. 3 is a top phantom view of an embodiment of the disclosure.
Figure 6:
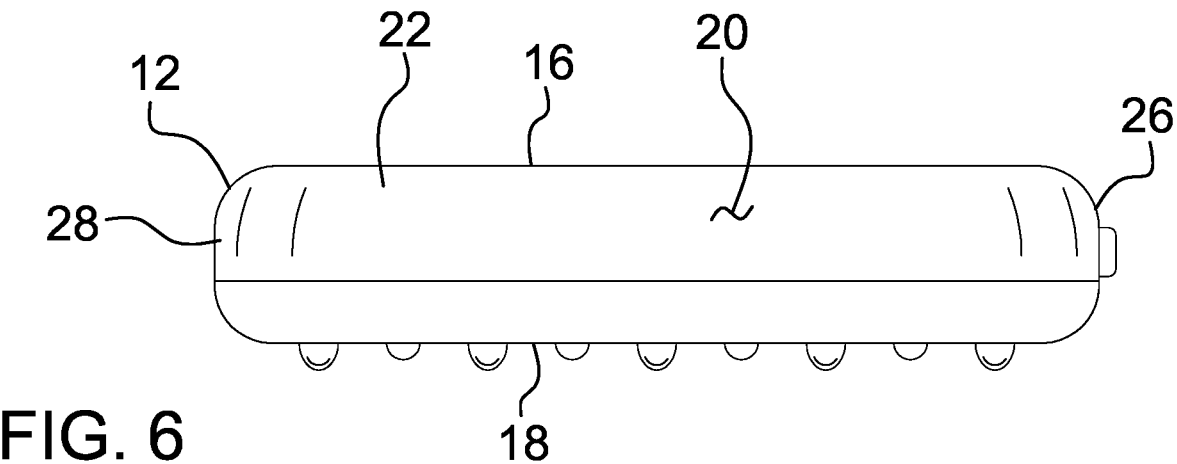
FIG. 6 is a front view of an embodiment of the disclosure.
Figure 7:
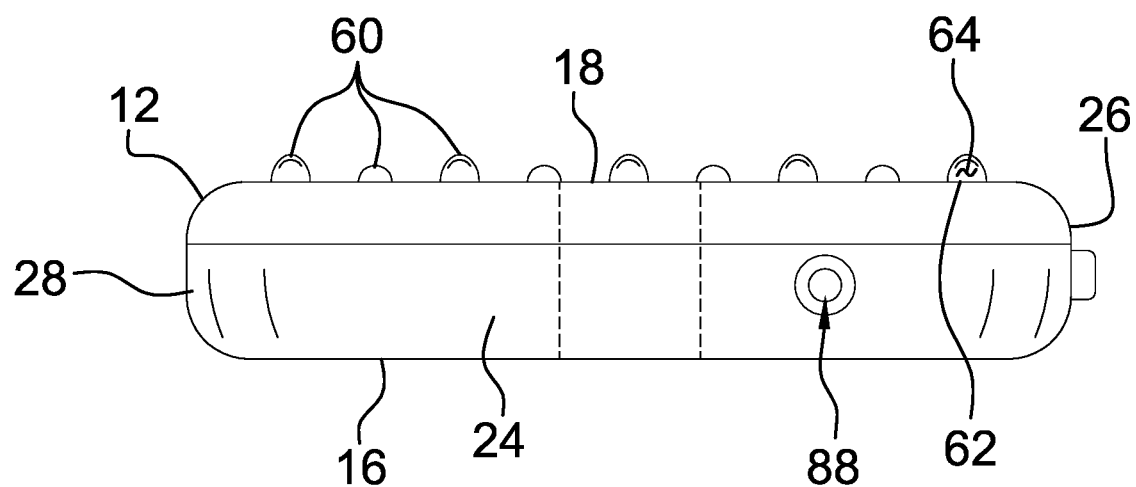
FIG. 7 is a back view of an embodiment of the disclosure.
Figure 8:
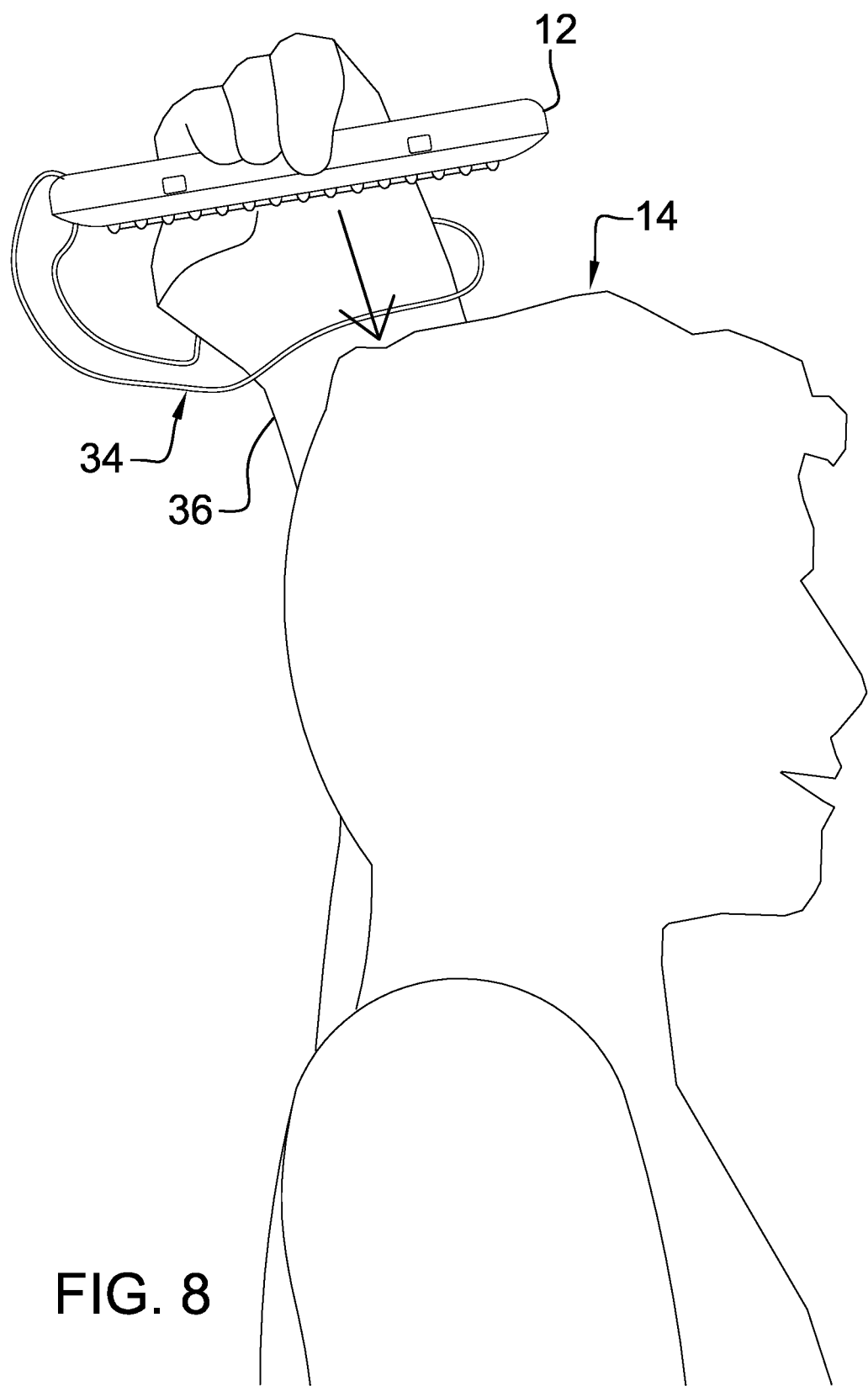
FIG. 8 is a perspective in-use view of an embodiment of the disclosure.

With reference now to the drawings, and in particular to FIGS. 1 through 8 thereof, a new stimulation device embodying the principles and concepts of an embodiment of the disclosure and generally designated by the reference numeral 10 will be described.

As best illustrated in FIGS. 1 through 8, the scalp stimulation assembly 10 generally comprises a panel 12 which is comprised of a fluid impermeable material thereby facilitating the panel 12 to be rubbed along a user's scalp 14 while bathing. The panel 12 has a top surface 16, a bottom surface 18 and a perimeter surface 20 extending between the top surface 16 and the bottom surface 18. The perimeter surface 20 has a front side 22, a back side 24, a first lateral side 26 and a second lateral side 28. The top surface 16 has a first well 30 extending toward the bottom surface 18 and the first well 30 is positioned adjacent to the back side 24. The bottom surface 18 has a second well 32 extending toward the top surface 16 and the second well 32 is aligned with the first well 30.

A wrist band 34 is provided that is removably attachable to the panel 12 such that the wrist band 34 can be worn around the user's wrist 36 for carrying the panel 12. The wrist band 34 comprises a closed ring 38 that can be worn around the user's wrist 36 and which has an outer surface 40. The wrist band 34 includes a band 42 that has a first end 44 and a second end 46, and the first end 44 is coupled to the outer surface 40 of the closed ring 38. The wrist band 34 includes a grip 48 comprising a central member 50 extending between a pair of outward members 52. Each of the outward members 52 is perpendicularly oriented with the central member 50 having the outward members 52 being spaced apart from each other. Additionally, each of the outward members 52 has a distal end 54 with respect to the central member 50.

The second end 46 of the band 42 is coupled to the central member 50 having each of the outward members 52 extending away from the band 42. Each of the outward members 52 has a tab 56 that is integrated into the outward members 52 and the tab 56 on each of the outward members 52 is positioned adjacent to the distal end 54 of a respective outward member. The tab 56 on each of the outward members 52 is directed toward each other. Moreover, the tab 56 on each of the outward members 52 engages a respective one of the first well 30 and the second well 32 for releasably retaining the wrist band 34 on the panel 12.

A plurality of light emitters 58 is provided and each of the light emitters 58 is coupled to the panel 12 to emit light onto the user's scalp 14 when the panel 12 is rubbed along the user's scalp 14. Each of the light emitters 58 has an operational frequency in the ultraviolet spectrum to stimulate hair growth on the user's scalp 14 when the panel 12 is rubbed along the user's scalp 14. Each of the light emitters 58 is positioned on the bottom surface 18 of the panel 12 and each of the light emitters 58 is elongated to extend substantially between the front side 22 and the back side 24 of the perimeter surface 20. Furthermore, the light emitters 58 are spaced apart from each other and are distributed between the first lateral side 26 and the second lateral side 28 of the perimeter surface 20. Each of the light emitters 58 may comprise a light emitting diode strip or the like.

A plurality of domes 60 is each coupled to the panel 12 such that each of the domes 60 frictionally engages the user's scalp 14 when the panel 12 is rubbed along the user's scalp 14 for stimulating hair growth. Each of the domes 60 has a lower surface 62 and an upper surface 64; the lower surface 62 is flattened and the upper surface 64 is convexly arcuate with respect to the lower surface 62. The lower surface 62 of each of the domes 60 is coupled to the top surface 16 of the panel 12. The plurality of domes 60 is arranged in a plurality of rows 66 each extending substantially between the front side 22 and the back side 24 of the perimeter surface 20 of the panel 12. Furthermore, each of the rows 66 is positioned adjacent to respective light emitters 58 such that the light emitters 58 and the rows 66 alternate between the first lateral side 26 and the second lateral side 28 of the perimeter surface 20. Each of the domes 60 is comprised of a resiliently compressible material wherein each of the domes 60 is configured to enhance comfort for the user. As is most clearly shown in FIGS. 6 and 7, the domes 60 associated with each of the rows 66 may have varying heights with respect to the panel 12 for enhanced stimulation of the user's scalp 14.

A control circuit 68 is integrated into the panel 12 and the control circuit 68 is electrically coupled to each of the light emitters 58. An electronic timer 70 is integrated into the panel 12 and the electronic timer 70 is electrically coupled to the control circuit 68. The electronic timer 70 counts down a pre-determined duration of time when the electronic timer 70 is turned on. Additionally, the control circuit 68 receives a de-actuate input when the electronic timer 70 completes counting down the pre-determined duration of time. Each of the light emitters 58 is turned off when the control circuit 68 receives the de-actuate input.

A vibration unit 72 is integrated into the panel 12 and the vibration unit 72 is in mechanical communication with the panel 12. The vibration unit 72 vibrates the panel 12 when the vibration unit 72 is turned on to physically stimulate the user's scalp 14 when the panel 12 is rubbed along the user's scalp 14. The vibration unit 72 is electrically coupled to the control circuit 68. Furthermore, the vibration unit 72 may comprise an electronic vibration unit that may include an electric motor and a cam that is rotatably coupled to the electric motor which rotates about an eccentric axis with respect to the electric motor.

A timer button 74 is movably integrated into the first lateral side 26 of the perimeter surface 20 of the panel 12 and the timer button 74 is electrically coupled to the control circuit 68. The electronic timer 70 is actuated to count down the pre-determined duration of time when the timer button 74 is depressed. An actuate button 76 is movably integrated into the first lateral side 26 of the perimeter surface 20 of the panel 12 and the actuate button 76 is electrically coupled to the control circuit 68. Each of the light emitters 58 is actuated to a minimum intensity when the actuate button 76 is depressed a corresponding number of times and each of the light emitters 58 is actuated to a medium intensity when the actuate button 76 is depressed a corresponding number of times. Continuing, each of the light emitters 58 is actuated to a maximum intensity when the actuate button 76 is depressed a corresponding number of times and each of the light emitters 58 is turned off when the actuate button 76 is depressed a corresponding number of times. Furthermore, the vibration unit 72 is turned on when the actuate button 76 is depressed a corresponding number of times and the vibration unit 72 is turned off when the actuate button 76 is depressed a corresponding number of times.

A power supply 78 is integrated into the panel 12 and the power supply 78 is electrically coupled to the control circuit 68. The power supply 78 comprises at least one battery 80 that is positioned within the housing and the at least one battery 80 is electrically coupled to the control circuit 68. As is most clearly shown in FIG. 3, a battery cover 82 is removably integrated into the bottom surface 18 of the panel 12 and the at least one battery 80 is positioned beneath the battery cover 82. Additionally, a gasket 84 may be positioned beneath the battery cover 82 to form a fluid impermeable seal between the battery cover 82 and the panel 12. Additionally, a pair of screws 86 may extend through the battery cover 82 and engage the panel 12 for retaining the battery cover 82 on the panel 12. The power supply 78 includes a charge port 88 that is recessed into the perimeter surface 20 of the panel 12 to receive a charge cord 90. The charge port 88 is electrically coupled to the at least one battery 80 for charging the at least one battery 80.

In use, the actuate button 76 is depressed a corresponding number of times to actuate the light emitters 58 to a desired intensity and to actuate the vibration unit 72. In this way the light emitters 58 emit ultraviolet light on the user's scalp 14 for stimulating hair growth when the panel 12 is rubbed along the user's scalp 14. Additionally, the domes 60 and the vibration unit 72 physically stimulate the user's scalp 14 for facilitating hair growth. In this way the user's scalp can be stimulated for treating hair loss, pattern baldness or other hair loss related conditions. The timer button 74 can be manipulated to automatically turn off the light emitters 58 and the vibration unit 72 after a pre-determined duration of time.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A scalp stimulation assembly for stimulating hair follicles to treat hair loss, said assembly comprising:
    a panel being comprised of a fluid impermeable material wherein said panel is configured to be rubbed along a user's scalp when the user is bathing;
    a wrist band being removably attachable to said panel wherein said wrist band is configured to be worn around the user's wrist for carrying said panel;
    a plurality of light emitters, each of said light emitters being coupled to said panel wherein each of said light emitters is configured to emit light onto the user's scalp when said panel is rubbed along the user's scalp, each of said light emitters having an operational frequency in the ultraviolet spectrum wherein each of said light emitters is configured to stimulate hair growth on the user's scalp when said panel is rubbed along the user's scalp;
    a plurality of domes, each of said domes being coupled to said panel wherein each of said domes is configured to frictionally engage the user's scalp when said panel is rubbed along the user's scalp for stimulating hair growth;
    a vibration unit being integrated into said panel, said vibration unit being in mechanical communication with said panel, said vibration unit vibrating said panel when said vibration unit is turned on wherein said vibration unit is configured to physically stimulate the user's scalp when said panel is rubbed along the user's scalp;
    wherein said panel has a top surface, a bottom surface and a perimeter surface extending between said top surface and said bottom surface, said perimeter surface having a front side, a back side, a first lateral side and a second lateral side, said top surface having a first well extending toward said bottom surface, said first well being positioned adjacent to said back side, said bottom surface having a second well extending toward said top surface, said second well being aligned with said first well;
    wherein each of said domes has a lower surface and an upper surface, said lower surface being flattened, said upper surface being convexly arcuate with respect to said lower surface, said lower surface of each of said domes being coupled to said top surface of said panel;
    wherein said plurality of domes is arranged in a plurality of rows each extending substantially between said front side and said back side of said perimeter surface of said panel, each of said rows being positioned adjacent to respective light emitters such that said light emitters and said rows alternate between said first lateral side and said second lateral side of said perimeter surface; and
    wherein each of said domes is comprised of a resiliently compressible material wherein each of said domes is configured to enhance comfort for the user.

2. The assembly according to claim 1, wherein said wrist band comprises:
    a closed ring having an outer surface wherein said closed ring is configured to be worn around the user's wrist;
    a band having a first end and a second end, said first end being coupled to said outer surface of said closed ring; and
    a grip comprising a central member extending between a pair of outward members, each of said outward members being perpendicularly oriented with said central member having said outward members being spaced apart from each other, each of said outward members having a distal end with respect to said central member, said second end of said band being coupled to said central member having each of said outward members extending away from said band, each of said outward members having a tab being integrated into said outward members, said tab on each of said outward members being positioned adjacent to said distal end of a respective outward member, said tab on each of said outward members being directed toward each other, said tab on each of said outward members engaging a respective one of said first well and said second well for releasably retaining said wrist band on said panel.

3. The assembly according to claim 1, wherein each of said light emitters is positioned on said bottom surface of said panel, each of said light emitters being elongated to extend substantially between said front side and said back side of said perimeter surface, said light emitters being spaced apart from each other and being distributed between said first lateral side and said second lateral side of said perimeter surface.

4. The assembly according to claim 1, further comprising:
    a control circuit being integrated into said panel, said control circuit being electrically coupled to each of said light emitters; and
    an electronic timer being integrated into said panel, said electronic timer being electrically coupled to said control circuit, said electronic timer counting down a pre-determined duration of time when said electronic timer is turned on, said control circuit receiving a de-actuate input when said electronic timer completes counting down said pre-determined duration of time, each of said light emitters being turned off when said control circuit receives said de-actuate input.

5. The assembly according to claim 4, further comprising:
    a timer button being movably integrated into said first lateral side of said perimeter surface of said panel, said timer button being electrically coupled to said control circuit, said electronic timer being actuated to count down said pre-determined duration of time when said timer button is depressed; and an actuate button being movably integrated into said first lateral side of said perimeter surface of said panel, said actuate button being electrically coupled to said control circuit, each of said light emitters being actuated to a minimum intensity when said actuate button is depressed a corresponding number of times, each of said light emitters being actuated to a medium intensity when said actuate button is depressed a corresponding number of times, each of said light emitters being actuated to a maximum intensity when said actuate button is depressed a corresponding number of times, each of said light emitters being turned off when said actuate button is depressed a corresponding number of times, said vibration unit being turned on when said actuate button is depressed a corresponding number of times, said vibration unit being turned off when said actuate button is depressed a corresponding number of times.

6. The assembly according to claim 4, further comprising a power supply being integrated into said panel, said power supply being electrically coupled to said control circuit, said power supply comprising:

at least one battery being positioned within said housing, said at least one battery being electrically coupled to said control circuit; and a charge port being recessed into said panel wherein said charge port is configured to be electrically coupled to a charge cord, said charge port being electrically coupled to said at least one battery for charging said at least one battery.

7. A scalp stimulation assembly for stimulating hair follicles to treat hair loss, said assembly comprising:

a panel being comprised of a fluid impermeable material wherein said panel is configured to be rubbed along a user's scalp when the user is bathing, said panel having a top surface, a bottom surface and a perimeter surface extending between said top surface and said bottom surface, said perimeter surface having a front side, a back side, a first lateral side and a second lateral side, said top surface having a first well extending toward said bottom surface, said first well being positioned adjacent to said back side, said bottom surface having a second well extending toward said top surface, said second well being aligned with said first well;

a wrist band being removably attachable to said panel wherein said wrist band is configured to be worn around the user's wrist for carrying said panel, said wrist band comprising:

a closed ring having an outer surface wherein said closed ring is configured to be worn around the user's wrist;

a band having a first end and a second end, said first end being coupled to said outer surface of said closed ring; and a grip comprising a central member extending between a pair of outward members, each of said outward members being perpendicularly oriented with said central member having said outward members being spaced apart from each other, each of said outward members having a distal end with respect to said central member, said second end of said band being coupled to said central member having each of said outward members extending away from said band, each of said outward members having a tab being integrated into said outward members, said tab on each of said outward members being positioned adjacent to said distal end of a respective outward member, said tab on each of said outward members being directed toward each other, said tab on each of said outward members engaging a respective one of said first well and said second well for releasably retaining said wrist band on said panel;

a plurality of light emitters, each of said light emitters being coupled to said panel wherein each of said light emitters is configured to emit light onto the user's scalp when said panel is rubbed along the user's scalp, each of said light emitters having an operational frequency in the ultraviolet spectrum wherein each of said light emitters is configured to stimulate hair growth on the user's scalp when said panel is rubbed along the user's scalp, each of said light emitters being positioned on said bottom surface of said panel, each of said light emitters being elongated to extend substantially between said front side and said back side of said perimeter surface, said light emitters being spaced apart from each other and being distributed between said first lateral side and said second lateral side of said perimeter surface;

a plurality of domes, each of said domes being coupled to said panel wherein each of said domes is configured to frictionally engage the user's scalp when said panel is rubbed along the user's scalp for stimulating hair growth, each of said domes having a lower surface and an upper surface, said lower surface being flattened, said upper surface being convexly arcuate with respect to said lower surface, said lower surface of each of said domes being coupled to said top surface of said panel, said plurality of domes being arranged in a plurality of rows each extending substantially between said front side and said back side of said perimeter surface of said panel, each of said rows being positioned adjacent to respective light emitters such that said light emitters and said rows alternate between said first lateral side and said second lateral side of said perimeter surface, each of said domes being comprised of a resiliently compressible material wherein each of said domes is configured to enhance comfort for the user;

a control circuit being integrated into said panel, said control circuit being electrically coupled to each of said light emitters;

an electronic timer being integrated into said panel, said electronic timer being electrically coupled to said control circuit, said electronic timer counting down a pre-determined duration of time when said electronic timer is turned on, said control circuit receiving a de-actuate input when said electronic timer completes counting down said pre-determined duration of time, each of said light emitters being turned off when said control circuit receives said de-actuate input;

a vibration unit being integrated into said panel, said vibration unit being in mechanical communication with said panel, said vibration unit vibrating said panel when said vibration unit is turned on wherein said vibration unit is configured to physically stimulate the user's scalp when said panel is rubbed along the user's scalp, said vibration unit being electrically coupled to said control circuit;

a timer button being movably integrated into said first lateral side of said perimeter surface of said panel, said timer button being electrically coupled to said control circuit, said electronic timer being actuated to count down said pre-determined duration of time when said timer button is depressed;

an actuate button being movably integrated into said first lateral side of said perimeter surface of said panel, said actuate button being electrically coupled to said control circuit, each of said light emitters being actuated to a minimum intensity when said actuate button is depressed a corresponding number of times, each of said light emitters being actuated to a medium intensity when said actuate button is depressed a corresponding number of times, each of said light emitters being actuated to a maximum intensity when said actuate button is depressed a corresponding number of times, each of said light emitters being turned off when said actuate button is depressed a corresponding number of times, said vibration unit being turned on when said actuate button is depressed a corresponding number of times, said vibration unit being turned off when said actuate button is depressed a corresponding number of times; and a power supply being integrated into said panel, said power supply being electrically coupled to said control circuit, said power supply comprising:
- at least one battery being positioned within said housing, said at least one battery being electrically coupled to said control circuit; and
- a charge port being recessed into said perimeter surface of said panel wherein said charge port is configured to be electrically coupled to a charge cord, said charge port being electrically coupled to said at least one battery for charging said at least one battery.

\* \* \* \* \*